United States Patent
Sunada et al.

(10) Patent No.: US 11,071,842 B2
(45) Date of Patent: Jul. 27, 2021

(54) LOW-FLOW OXYGEN THERAPY HUMIDIFIER AND METHOD

(71) Applicant: Perma Pure LLC, Lakewood, NJ (US)

(72) Inventors: Craig Sunada, Manasquan, NJ (US);
Wanchai Lim, Lakewood, NJ (US);
Nate Inkrote, Lakewood, NJ (US);
Steven Lepke, Wakefield, MA (US);
Vincent Lambert, Lakewood, NJ (US);
Eric Hyman, Lakewood, NJ (US);
Wayne S. Breyer, Middletown, NJ (US)

(73) Assignee: Perma Pure LLC, Lakewood, NJ (US)

( * ) Notice: Subject to any disclaimer, the term of this patent is extended or adjusted under 35 U.S.C. 154(b) by 384 days.

(21) Appl. No.: 16/053,531

(22) Filed: Aug. 2, 2018

(65) Prior Publication Data
US 2020/0009348 A1    Jan. 9, 2020

Related U.S. Application Data

(60) Provisional application No. 62/695,661, filed on Jul. 9, 2018.

(51) Int. Cl.
*A61M 16/14*    (2006.01)
*A61M 16/10*    (2006.01)
*A61M 16/16*    (2006.01)

(52) U.S. Cl.
CPC ...... *A61M 16/142* (2014.02); *A61M 16/1005* (2014.02); *A61M 16/109* (2014.02); *A61M 16/1095* (2014.02); *A61M 16/164* (2014.02); *A61M 2202/0208* (2013.01); *A61M 2205/3653* (2013.01); *A61M 2205/60* (2013.01); *A61M 2205/8262* (2013.01)

(58) Field of Classification Search
CPC .. A61M 16/142; A61M 16/147; A61M 16/16; A61M 16/1046; A61M 16/1005; A61M 16/164; A61M 16/109; A61M 16/1095; A61M 2205/7536; A61M 16/1045; F24F 6/10
See application file for complete search history.

(56) References Cited

U.S. PATENT DOCUMENTS 4,861,523 A * 8/1989 Beran ............... A61M 16/16
261/104
4,921,642 A 5/1990 LaTorraca
(Continued)

FOREIGN PATENT DOCUMENTS

| WO | 98/48873 A1 | 11/1998 |
| WO | 2006/041483 A1 | 4/2006 |
| WO | 2014/006574 A1 | 1/2014 |

OTHER PUBLICATIONS

Perma Pure, "Nafion Tubing", http://permapure.com/products/nafion-tubing/, May 31, 2019.
(Continued)

*Primary Examiner* — Joseph D. Boecker
*Assistant Examiner* — Thomas W Greig
(74) *Attorney, Agent, or Firm* — Kaplan Breyer Schwarz, LLP

(57) ABSTRACT

A system for humidifying oxygen for low-flow oxygen therapy includes a volume-adaptable water reservoir that contains, in addition to water, a water-vapor-permeable membrane.

29 Claims, 10 Drawing Sheets

(56) References Cited

U.S. PATENT DOCUMENTS

| | | | |
|---|---|---|---|
| 4,943,704 | A | 7/1990 | Rabenau et al. |
| 5,970,210 | A | 10/1999 | Anthony |
| 6,584,972 | B2 * | 7/2003 | McPhee ............ A61M 16/0841 |
| | | | 128/203.17 |
| 7,708,013 | B2 | 5/2010 | Niland et al. |
| 9,114,225 | B1 | 8/2015 | Roberts et al. |
| 10,350,376 | B2 * | 7/2019 | White ............... A61M 16/0622 |
| 2006/0021615 | A1 | 2/2006 | Kertzman |
| 2009/0000620 | A1 * | 1/2009 | Virr .................... A61M 16/142 |
| | | | 128/203.27 |
| 2010/0059053 | A1 | 3/2010 | Niland |
| 2012/0125333 | A1 | 5/2012 | Bedford et al. |
| 2015/0090260 | A1 | 4/2015 | Seakins et al. |
| 2015/0328431 | A1 | 5/2015 | Arcilla et al. |
| 2016/0287832 | A1 * | 10/2016 | Cortez, Jr. ........ A61M 16/0057 |
| 2017/0095635 | A1 * | 4/2017 | Huby ................. A61M 16/024 |

OTHER PUBLICATIONS

Extended European Search Report issued in EP Patent Application No. 19183988.5 dated Dec. 11, 2019.
English Translation of Office Action dated Jan. 6, 2021 in Chinese Patent Application No. 201910609482.3.
Office Action issued in counterpart Chinese patent application No. 201921062171.1, dated Mar. 12, 2020, 4 pp.

\* cited by examiner

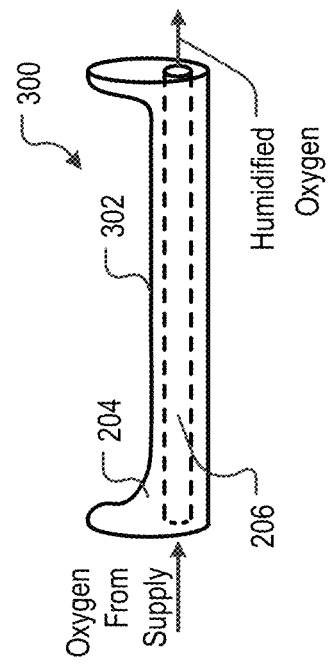
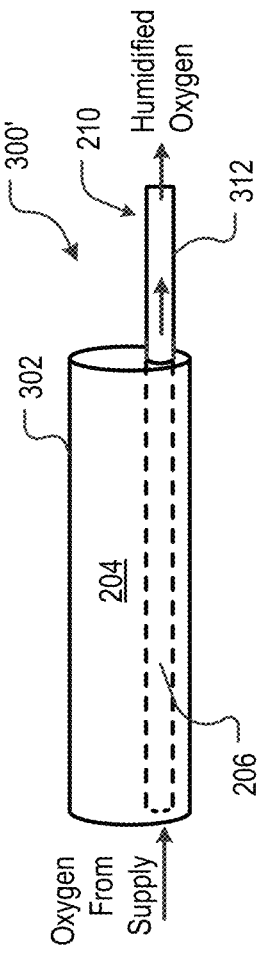
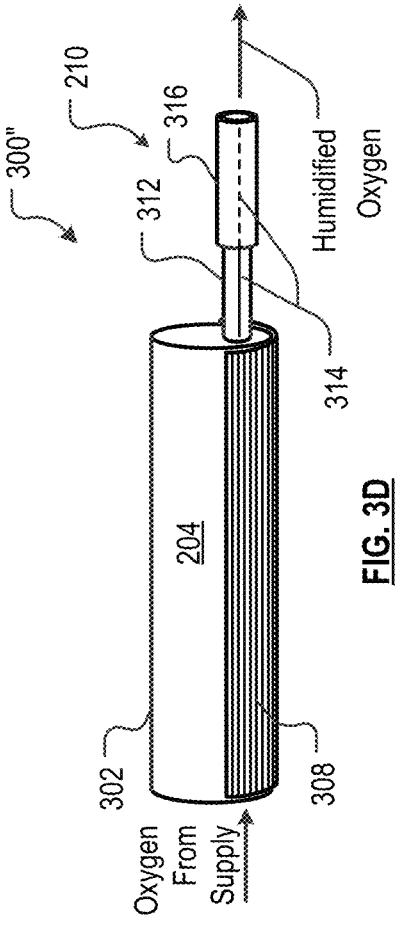

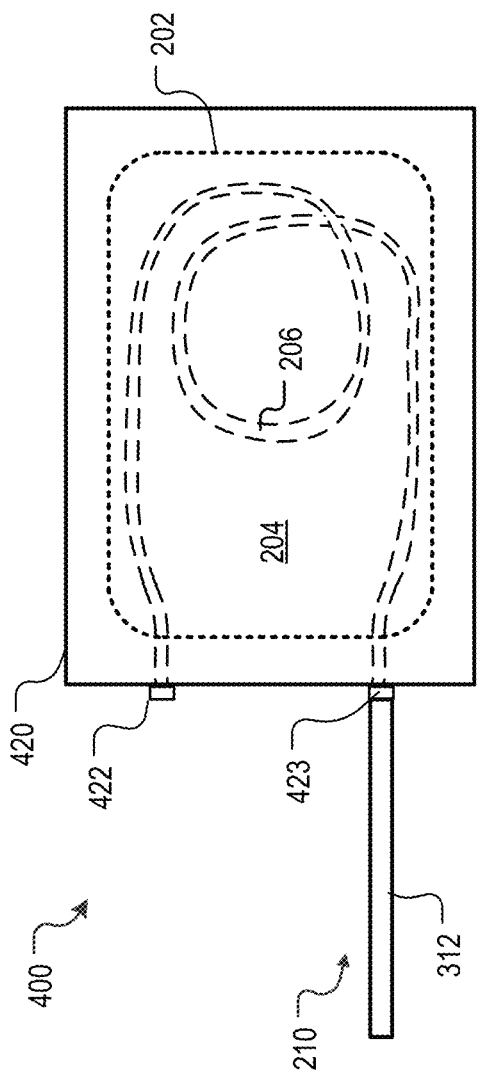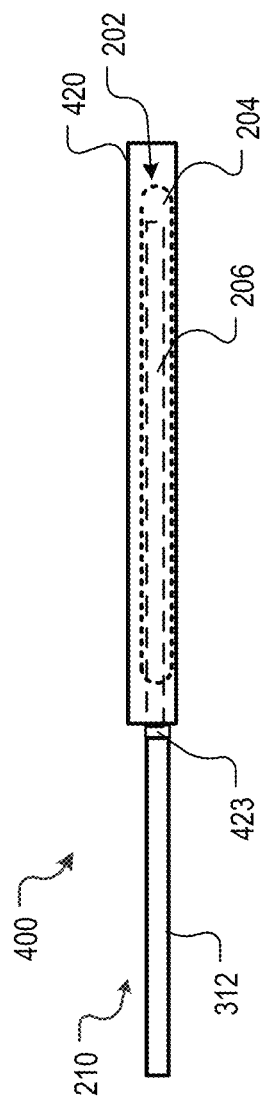

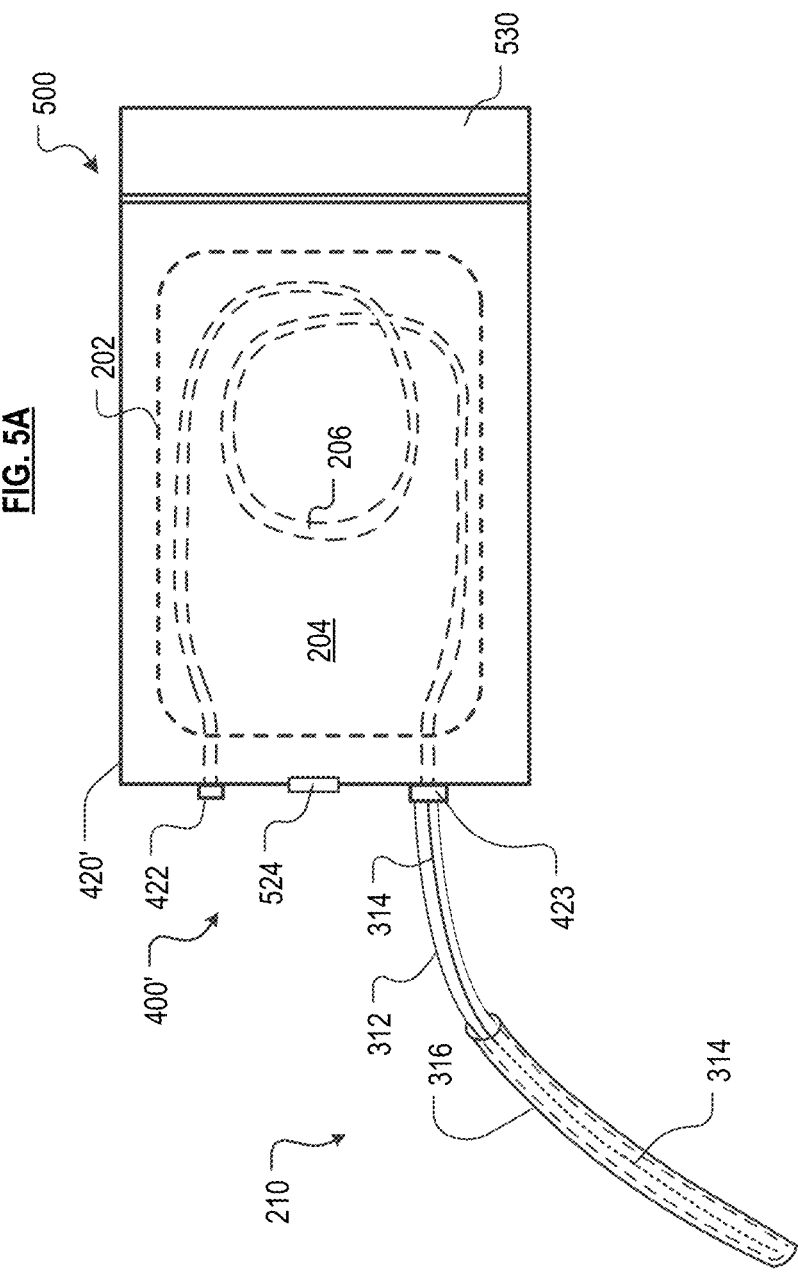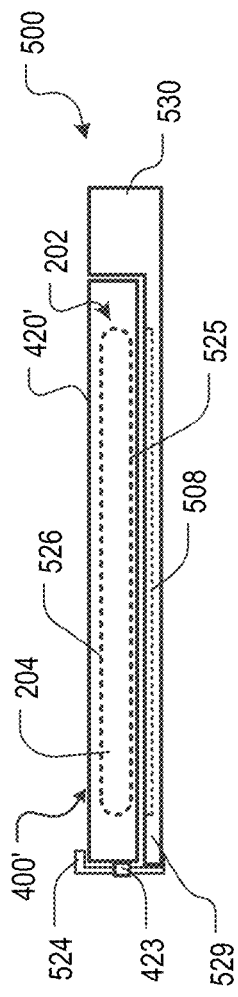
FIG. 5A
FIG. 5B

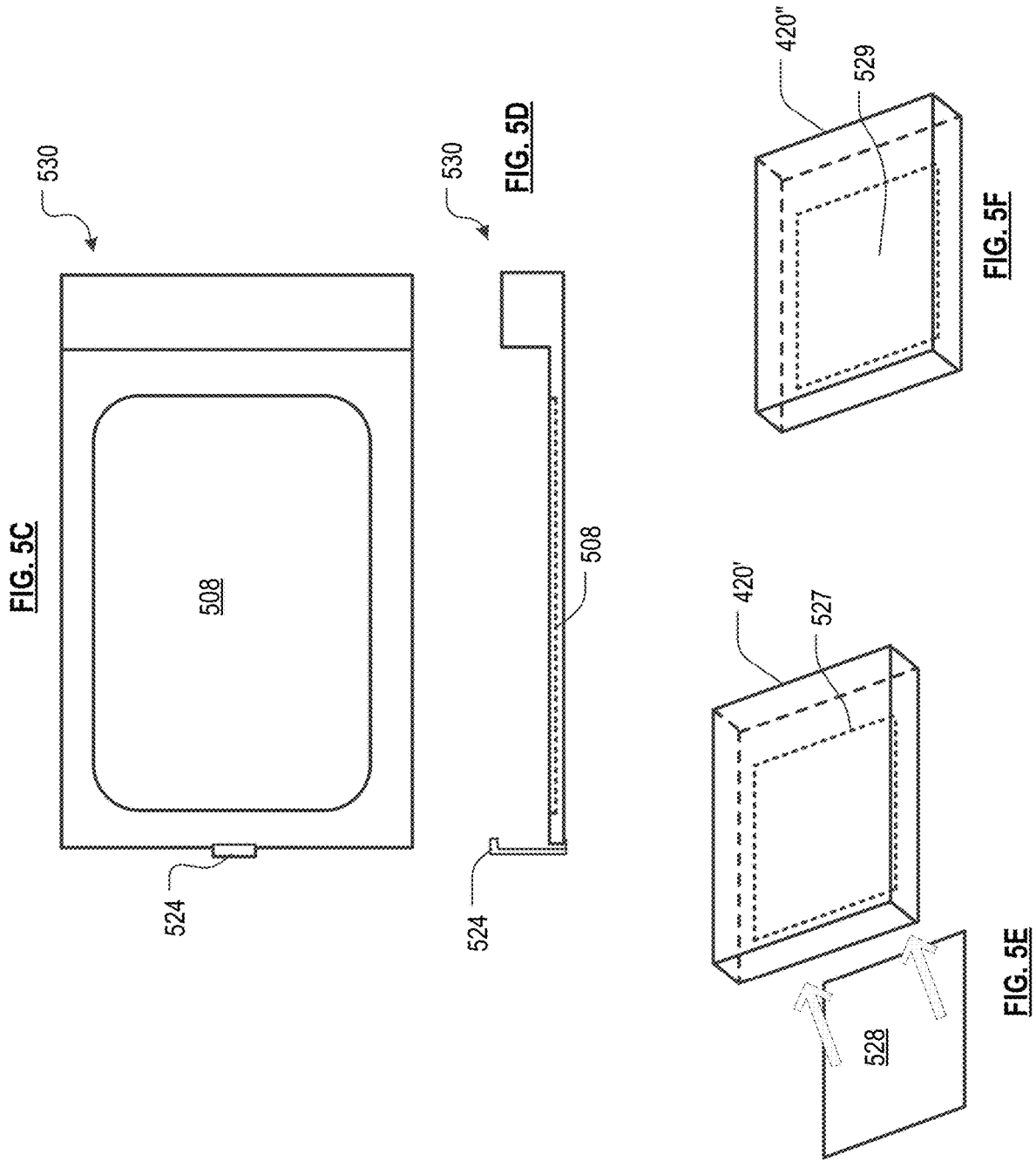

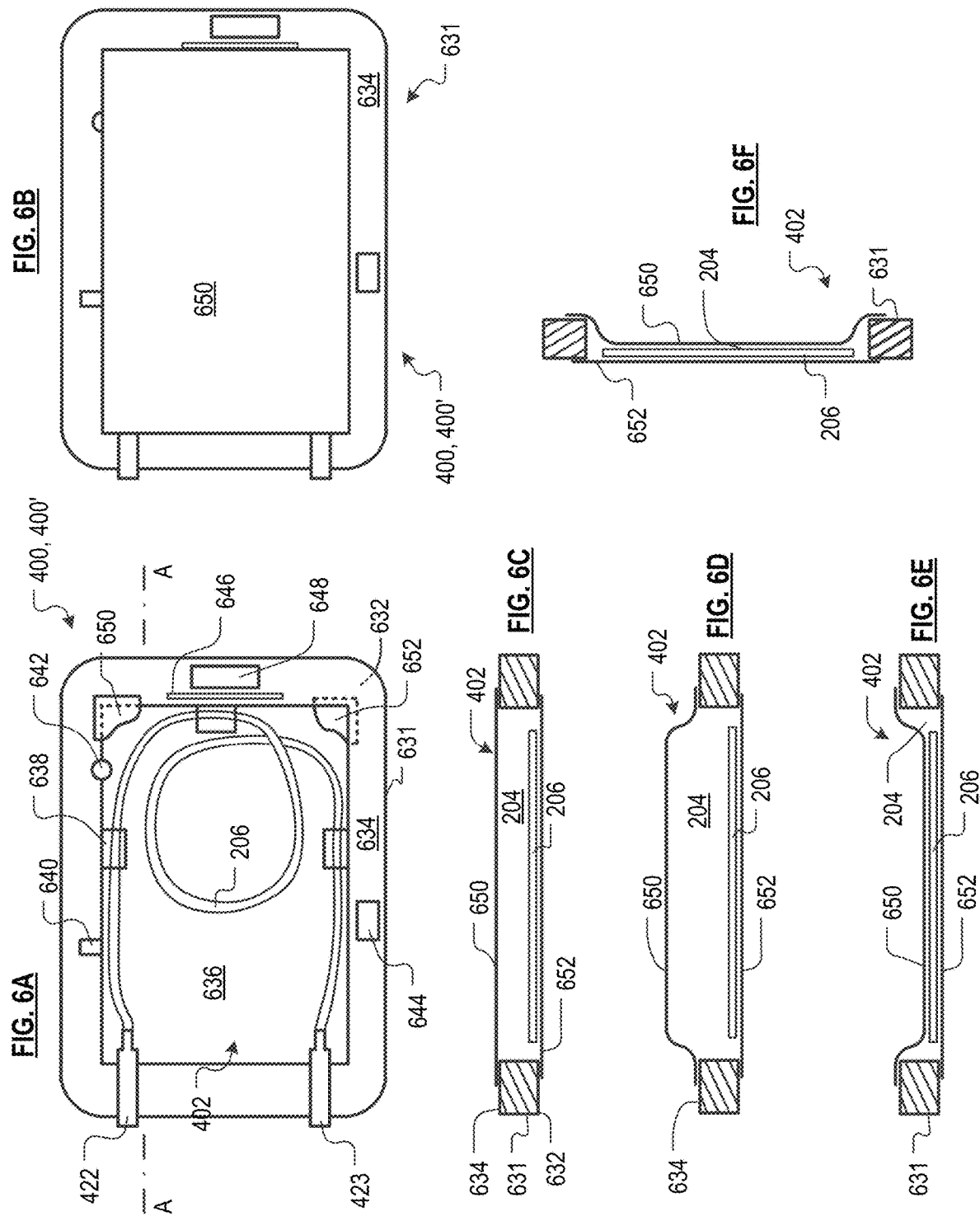

LOW-FLOW OXYGEN THERAPY HUMIDIFIER AND METHOD

FIELD OF THE INVENTION

The present invention relates to low-flow oxygen therapy.

BACKGROUND OF THE INVENTION

Administering oxygen to increase arterial oxygenation is a common clinical intervention for a patient in respiratory distress. Supplemental oxygen is provided by an oxygen delivery system, which entrains oxygen in air. These systems are typically classified as being "low flow" or "high flow." The former type of system provides oxygen at a rate that is lower than a patient's inspiratory demands, while the latter provides oxygen at a rate that is higher.

An adult patient receives about 1-6 liters per minute of oxygen during low-flow therapy. Untreated oxygen is cold and dry, which will cause a patient's airway to lose moisture, resulting in the drying of the nose, throat, lips, and lungs. In addition to being a source of discomfort, such drying can also result in nasal tissue trauma and infection. For these reasons, water vapor is added to the supplied oxygen to humidify it, typically through a device called a "bubbler." The humidified air is not heated in standard low flow oxygen therapy.

Before it is inspired, the humidified oxygen travels through two conduits: a nasal cannula and a conduit that delivers the oxygen thereto. As it traverses these conduits, heat is lost from humidified oxygen, resulting in condensation—so called "rain out"— of some of the added moisture. Such liquid water, which accumulates in the conduit and cannula, provides a medium for bacterial growth. And the bacteria in the water can be transferred to the oxygen and then to the patient. Additionally, the flowing oxygen can carry water droplets directly into the patient's nose. Moreover, due to rain out and the unheated bubbler, the level of humidification is below that required for comfort for many patients. To this end, a heating element is often incorporated in the conduit that delivers the oxygen to the nasal cannula.

The prior art is replete with humidification systems for oxygen therapy. Most patients requiring oxygen therapy are relatively immobile. Consequently, most humidification systems for oxygen therapy are not portable. There are, however, certain health conditions requiring low-flow oxygen therapy in which the patient is somewhat mobile, at least briefly (i.e., several hours). To the extent that any portable prior-art humidification systems exist, they have met with limited commercial acceptance. This is due to a variety of technical and ergonomic issues. A need therefore remains for improvements to humidification solutions for low-flow oxygen therapy systems.

SUMMARY OF THE INVENTION

The present invention provides a system and method for humidifying oxygen for low-flow oxygen therapy while avoiding drawbacks of the prior art. Some embodiments of the invention are capable of providing humidified oxygen at flow rates in the range of about 0.5 to about 6 liters per minute without rain-out in the line that delivers humidified oxygen to the patient. The system has a small, portable form factor that enables it to be comfortably worn by a patient. In some embodiments, the humidification system is sufficiently self-contained to be portable.

Some embodiments of a humidification system in accordance with the present teachings include: (1) a reservoir that contains (at least during operation of the system) water, and, in addition, (2) a water-vapor-permeable (WVP) membrane. The WVP membrane, which in the illustrative embodiments is in the form of tubing, is disposed within the reservoir. During operation, the WVP membrane fluidically couples to a source of oxygen. The WVP membrane permits water vapor, but not liquid water, to pass from the reservoir into the WVP membrane, thereby humidifying the oxygen flowing therein. In the illustrative embodiment, the WVP membrane comprises Nafion™ tubing.

In some embodiments, the humidification system is structured so that the WVP membrane remains in contact with liquid water as long as some minimum amount of water is present in the reservoir. Liquid-water contact (as opposed to water vapor) with the WVP membrane results in best humidification performance. To accomplish this, the reservoir is able to alter its capacity/volume to substantially match the volume of the water present in the reservoir (plus the volume of the WVP membrane within the reservoir). Structural adaptations that facilitate this capability are described later in this specification. In some of such embodiments, contact between the WVP membrane and the water is maintained regardless of the spatial orientation of the reservoir (e.g., vertical as opposed to horizontal, etc.). This is facilitated by restraints that maintain the WVP membrane at a fixed location in the reservoir, in addition to the structural adaptations that enable the reservoir to alter its volume.

In some embodiments, the water reservoir is refillable. In some embodiments, the system includes a heating element for heating the water in the reservoir, thereby controlling the amount to which the oxygen is humidified. In some embodiments, an outlet conduit carrying the oxygen humidified by the system includes a heating element for heating the humidified oxygen. In some embodiments, the level of heating provided to the water reservoir and the outlet conduit can be varied by a user.

The humidification system may be embodied in a variety of form factors. For example, in some embodiments, the humidification system comprises a tubular WVP membrane within an outer tube, the outer tube functioning as the reservoir.

In some other embodiments, the humidification system comprises a housing having a thin, flat profile, wherein the housing contains at least the reservoir and the WVP tubular membrane. When so embodied, the humidification system is characterized as a "cartridge." Within the cartridge, the reservoir is embodied in any one of a number of different forms, some of which are disclosed herein. In some embodiments in which the reservoir is heated, the heating element is not contained within the cartridge. In some of such embodiments, the heating element is contained in a separate structure referred to as a "receiver," which is structurally arranged to physically couple to the cartridge. When so coupled, the heating element in the receiver and the reservoir in the cartridge are situated to facilitate heat transfer from the heating element to the reservoir.

Summarizing, the humidification system, as depicted and described, comprises: (i) a reservoir, and (ii) a WVP membrane, wherein the latter is disposed at least partially in the former. Embodiments of the humidification system may further comprise at least one of the following features, in any (non-conflicting) combination, among other features disclosed herein:

The humidification system is structurally configured to ensure that the WVP membrane within the reservoir remains in contact with liquid water.

The humidification system is structurally configured to ensure that the WVP membrane within the reservoir remains in contact with liquid water regardless of the spatial orientation of the reservoir.

The reservoir is structurally configured to adapt its volume to the amount of liquid water contained therein, wherein the adapted reservoir volume is substantially equal to the volume of the WVP membrane in the reservoir and the volume of the liquid water remaining in the reservoir.

The reservoir comprises two spaced-apart liquid-water-impermeable membranes, wherein a first one of the two membranes comprises a greater surface area than a second one of the two membranes.

The reservoir comprises a pouch.

The reservoir comprises a tube comprising a soft, pliable material.

The reservoir is heated.

A user can control the amount of heating applied to the reservoir.

The system includes a user interface by which a user adjusts the temperature of the reservoir.

The reservoir is vented.

The reservoir is refillable.

The system includes a means for applying positive pressure to the reservoir.

The WVP membrane comprises a perfluorosulfonic acid polymer.

The humidification system includes an oxygen outlet line.

The oxygen outlet line is heated.

A user can control the amount of heating applied to the oxygen outlet line.

The humidification system includes a power source.

The reservoir and the tube are contained in housing, wherein the housing, reservoir, and tube collectively define a cartridge.

The cartridge includes an identifier that is electronically read.

The housing includes a cover that detachably couples to the housing.

The system includes a receiver, wherein the receiver includes a heater, and wherein the receiver and a cartridge (as defined above) are physically adapted to couple to one another, and when coupled, the heater aligns with and is in sufficient proximity to the reservoir to heat the water therein.

A portion of the humidification system is disposable/replaceable.

BRIEF DESCRIPTION OF THE DRAWINGS

FIGS. 3A and 3B depict humidification system 300, which is an embodiment of humidification system 100 of FIG. 2.

FIG. 3C depicts humidification system 300', which is an embodiment of humidification system 100 of FIG. 2.

FIG. 3D depicts humidification system 300", which is an embodiment of humidification system 100 of FIG. 2.

FIGS. 4A and 4B depict respective top and side views of humidification system 400, which is an embodiment of humidification 100 of FIG. 2.

FIGS. 5A and 5B depict respective top and side views of humidification system 500, which is an embodiment of humidification 100 of FIG. 2.

FIGS. 5C and 5D depict respective top and side views of receiver 530 of humidification system 500.

FIGS. 5E and 5F depict perspective views of respective housings 420' and 420" for covering portions of the humidification system 500.

FIG. 6A depicts a top view, sans housing, of an embodiment of internal elements of cartridge 400 (humidification system 400) and cartridge 400' (humidification system 500).

FIG. 6B depicts the top view of FIG. 6A, showing upper membrane 650 of the reservoir in its entirety.

FIG. 6C depicts a sectional view, at line A-A, of the embodiment depicted in FIG. 6A, showing an embodiment of reservoir 202, wherein the reservoir is in a first state.

FIG. 6D depicts the reservoir of FIG. 6D in a second state.

FIG. 6E depicts the water reservoir of FIG. 6C in a third state.

FIG. 6F depicts the water reservoir in the third state, as in FIG. 6E, with the reservoir oriented vertically.

DETAILED DESCRIPTION

Figure 1:
FIG. 1 depicts a block diagram showing humidification system 100 in accordance with the present teachings in use in conjunction with a low-flow oxygen therapy system.

FIG. 1 depicts humidification system 100 in accordance with the present teachings, in use, receiving cool dry oxygen 92 from oxygen source 90 and delivering humidified oxygen 94, or heated, humidified oxygen 96, to nasal cannula 98. In the illustrative embodiment, humidification system 100 provides sufficient humidification (as discussed below) for oxygen flow rates in the range of about 0.5 to about 6.0 liters per minute (lpm). Oxygen source 90 may be a canister of oxygen or an oxygen concentrator. Neither the oxygen source 90 nor nasal cannula 98 are part of the present invention.

In some embodiments, based on the manner in which humidification system 100 operates, the dew point of the humidified oxygen is the temperature of the water used for humidification. In some embodiments of humidification system 100, the water used for humidifying the oxygen is heated, typically to a temperature in the range of about 28 to about 37° C. As a consequence, in such embodiments, humidification system 100 provides humidified oxygen 94 having a dew point in the range of about 28 to about 37° C. In some other embodiments, the water used for humidifying oxygen is not heated. Since evaporation of liquid (in this case, water) releases heat (i.e., latent energy), such unheated water cools to a temperature that is less than that of its surroundings.

After humidification, humidified oxygen 94 is conveyed to the patient. To that end, humidification system 100 is fluidically coupled to standard nasal cannula 98, as is widely available in the marketplace. In some embodiments, humidification system 100 includes an oxygen outlet line, which couples to nasal cannula 98. In some alternative embodiments, a proprietary cannula is used, which serves the function of both the oxygen outlet line and the nasal cannula.

There is usually at least a meter of cannula between humidification system 100 and the patient. If the water that humidifies the oxygen is not heated, then rain-out (condensation) will not occur in the cannula. This is because the dew point of humidified oxygen 94 (based on the aforementioned cooling phenomena) will be lower than the ambient temperature and, hence, lower than the temperature in the cannula. However, if the water is heated during the humidification process, then the dew point of humidified oxygen 94 will be greater than the ambient temperature. Consequently, as humidified oxygen 94 passes through the cannula, it will cool below its dew point and rain-out will occur.

To prevent rain-out, in some embodiments, the temperature of the humidified oxygen is increased above its dew point temperature (i.e., above 28-37° C.) via a source of heat. In some embodiments, the heating occurs in the oxygen outlet line (in such cases, the oxygen outlet line is commonly referred to as a "heated line"). In some embodiments, the temperature of humidified oxygen 96 is increased to a temperature in the range of about 37 to about 40° C.

Figure 2:
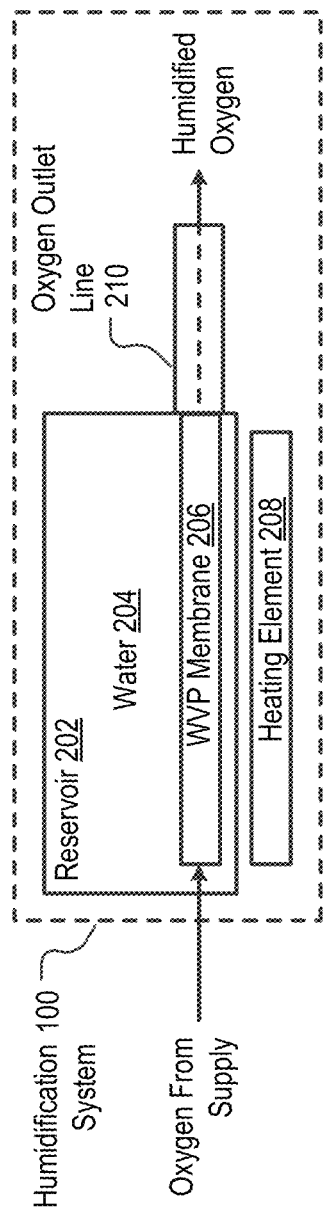
FIG. 2 depicts humidification system 100 in accordance with the present teachings.

FIG. 2 depicts humidification system 100 in accordance with the present teachings. Humidification system 100 includes reservoir 202, water-vapor-permeable (WVP) membrane 206, optional heating element 208, and optional oxygen outlet line 210.

During operation, reservoir 202 contains liquid water 204, which is either distilled or de-ionized. Liquid water 204 is the source for the humidity—water vapor—that is added to oxygen 92 coming from the oxygen supply.

As described later in this specification, reservoir 202 can be embodied in a variety of ways. For example, in some embodiments, the reservoir is in the form of a sealed "bag" or "pouch" filled with water. In some embodiments, the pouch of water is "single use," such that when the amount of water in reservoir drops below a threshold amount, the pouch is exchanged for another that is full of water. In some other embodiments, the pouch includes a re-sealable water fill port by which the pouch is refilled as liquid water evaporates. After a period of time, the refillable pouch is replaced to ensure consistent performance.

In some additional embodiments, reservoir 202 is in the form of a tube. In yet some further embodiments, the reservoir is embodied by a frame, having a central opening (the frame has an annular or ring shape, etc.), wherein water impermeable membranes seal each of the two major sides of the frame, thereby creating a void therebetween. In some embodiments, the void is filled with water via a re-sealable water fill port.

In the illustrative embodiments, WVP membrane 206 is in the form of a tube, which is situated either in whole or in major part, in reservoir 202. One end of the WVP tube is in fluidic communication with oxygen source 90, receiving dry oxygen therefrom, and the other end of the WVP tube is in fluidic communication with nasal cannula 98, providing humidified oxygen thereto. Oxygen flows through the inside of WVP membrane 206; the exterior of WVP membrane is exposed to water 204 that is within reservoir 202. Water vapor, sourced from liquid water 204, passes through WVP membrane 206 into the flowing oxygen, thereby humidifying it. Importantly, liquid water does not pass through the WVP membrane.

In some embodiments, WVP membrane 206 comprises a perfluorosulfonic acid (PFSA) polymer. Such polymers have a poly(tetrafluoroethylene) backbone with perfluoroether pendant side chains terminated by sulfonic acid groups. A preferred PFSA membrane for use in conjunction with the present invention is Nafion™, which is generated by the free-radical initiated copolymerization of a perfluorinated vinyl ether sulfonyl fluoride co-monomer with tetrafluoroethylene:

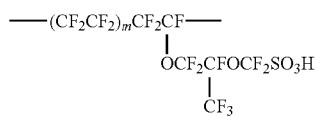

Nafion™ is highly selectively and exceedingly permeable to water vapor, yet does not allow oxygen and other gasses to pass through the membrane. Nafion™ is available from Perma Pure LLC of Lakewood, N.J.

Assuming a sufficient amount of Nafion™ is present (the sufficiency of which primarily being a function of the oxygen flow rate), the dew point of the humidified oxygen is equal to the temperature of the water at the surface of the Nafion™. At the prevailing oxygen flow rates (i.e., 0.5 to about 0.6 LPM), at least about 30 centimeters (cm) of TT-110 Nafion™ (http://permapure.com/products/nafion-tubing/) is sufficient to achieve the aforementioned humidification performance.

In some embodiments, WVP membrane 206 comprises a porous membrane that is permeable to water vapor but relatively impermeable to liquid water. Such WVP membranes include olefin-fiber membranes such as Tyvek, porous PTFE membranes such as Gore-tex and polysulfone hollow-fiber membranes. When using a porous membrane, additional design considerations are required to prevent water breakthrough. These considerations can include controlling the water pressure, increasing membrane thickness or various hydroscopic coatings or surface modifications. Porous membranes are typically permeable to oxygen and other gases, and careful management of the pressure differential from the inside to the outside of the tubing is required to prevent excessive transfer of oxygen through the tubing walls. For guidance, see, for example, U.S. Pat. No. 7,708,013, wherein a plurality of hollow-fiber membranes are used to humidify oxygen.

In some embodiments, WVP membrane 206 comprises a solid wall pervaporation membrane that selectively permeates water. Such materials include, for example, cellulose acetate, polyvinyl alcohol, polyimides and polyamides. The disadvantage of these membranes compared with Nafion™ include the need for significantly more surface area to achieve the same humidification levels, and poorer control over the final humidification level. Nafion™ can equalize the outlet dew point with the water temperature, while due to permeation resistance in the walls of other pervaporation membranes, the outlet dew point might not reach the same level. In addition, the bacteriostatic nature of Nafion™ prevents bacteria growth, while many of these materials can actively promote bacteria growth.

Liquid-water contact (as opposed to water vapor) with WVP membrane 206 results in best humidification performance. To that end, in some embodiments, reservoir 202 includes physical adaptations to ensure that, as water leaves the reservoir (i.e., from evaporation and transport of the vapor across WVP membrane 206), the reservoir "collapses," adapting its volume to the amount of liquid water remaining in the reservoir. This, in addition to any other physical adaptations, ensures that as long as a threshold amount of liquid water is present in reservoir 202, WVP membrane 206 remains in at least partial contact with liquid water 204. In some embodiments, the aforementioned threshold or minimal amount of liquid water is an amount sufficient to keep at least about ⅓ of the exterior surface area of WVP membrane 206 in contact with liquid water.

The ability of reservoir 202 to adapt its volume to the amount of liquid water is implemented by one or more features. One such feature is the presence of vent, which vents any air that enters the reservoir. Another such feature is the manner in which the reservoir is formed. In particular, in embodiments in which the reservoir comprises membranes attached to a frame, the upper membrane is vacuum formed into a shape that results in minimal space in the reservoir, similar to the shape shown in FIG. 3B. As a consequence, the upper membrane returns to this shape as water is removed from the reservoir. In addition, the area of the "upper" membrane will thus be greater than if it were simply pulled taut over the frame. This excess amount of membrane is sufficient to enable the reservoir to enlarge or contract, by movement of the upper membrane in response to the volume of water even if the upper membrane is flexible but not resilient (see, e.g., FIGS. 6D and 6E). In yet another embodiment, a bellows (i.e., flexible bag whose volume can be changed by compression or expansion) can be used to enable the reservoir to contract as the volume of water decreases.

Figure 8:
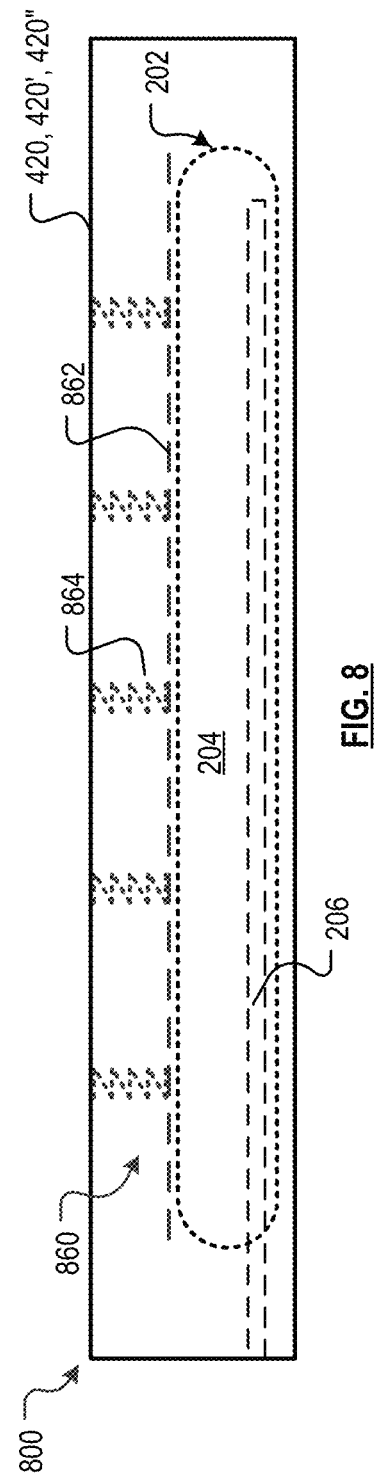
FIG. 8 depicts a side view of humidification system 800, which is an embodiment of humidification system 100 of FIG. 2.

In some embodiments, another structural adaptation the enables reservoir 202 to adapt its volume to the amount of liquid water present is an arrangement that applies a constant positive pressure to reservoir 202 (see, e.g., FIG. 8). In addition to its applicability to the aforementioned embodiments of reservoir 202, embodiments that include an arrangement for applying positive pressure can utilize a reservoir formed from two spaced-apart membranes and a frame wherein the upper membrane comprises a resilient material. The membrane will be capable of expanding to accommodate a maximum volume of water and, as liquid water in the reservoir decreases, the surface of the membrane will be capable of being forced "downward" (i.e., toward the "bottom" of the reservoir) due to the positive pressure, thereby reducing the volume of the reservoir.

In some embodiments, the same and, in some embodiments, one or more additional structural adaptations ensure that, as long as the aforementioned threshold amount of liquid water is present in reservoir 202, contact between WVP membrane 206 and liquid water 204 is maintained regardless of the orientation of reservoir 202 (e.g., horizontal, vertical, etc.). In some embodiments, an additional structural adaptation for this purpose comprises restraints that immobilize WVP membrane 206 and maintain it in a predetermined location within the reservoir.

Heating element 208, which is an optional element of humidification system 100, heats water 204 in reservoir 202. The heating element can take any form suitable for the form factor of reservoir 202. The heating element can be, for example and without limitation, a flat plate, a flexible tape/web of metal or wires, cartridge heater, or other conventional heating devices. The heat supplied by heating element 208 controls the level of humidification and the dew point of the oxygen. More particularly, heating the water in reservoir 202 as well as the oxygen flowing through WVP membrane 206 increases the level of humidification and, hence, the dew point of the flowing oxygen. In some embodiments, heating element 208 is resistively heated by electrical current, as may be sourced from an external source of power (e.g., AC power, as appropriately converted to DC and reduced in voltage, a battery, etc.), or via a power supply that is included in humidification system 100 (e.g., rechargeable or non-rechargeable battery, super capacitor, etc.).

Oxygen outlet line 210, which is an optional element of humidification system 100, receives humidified oxygen from WVP membrane 206. In some embodiments, oxygen outlet line 210 conveys the humidified oxygen to nasal cannula 98.

In some embodiments, particularly those in which water 204 in the reservoir is heated, oxygen outlet line 210 is heated as well via a heating element (not depicted in FIG. 2). The heating element can take any form suitable for the form factor of oxygen-outlet line 210, such as a wire, a flexible tape/web, etc. As described in further detail later in this specification, in some embodiments, the heating element for oxygen outlet line 210 comprises a carbon-fiber wire. In some embodiments in which oxygen outlet line 210 is heated, it includes a layer of insulation. Further description of oxygen outline line 210, in particular embodiments in which the line is heated, is provided later in this specification.

If a standard nasal cannula is used in conjunction with oxygen outlet line 210, an excess length of cannula may be present (i.e., beyond the meter or so required to traverse the distance between the outlet of oxygen outlet line 210 and the patient's nose). In embodiments in which oxygen outlet line 210 is heated, such excess length of cannula should be treated to prevent heat loss and condensation. In some embodiments, the cannula is insulated to minimize heat loss, such as can be accomplished by a "cozy" that wraps around the cannula. In some other embodiments, the nasal cannula itself is heated, such as by incorporating a heating element in/on the cannula or in the cozy.

In some embodiments, heating element 208 for water 204 in reservoir 202 also functions as the heat source for the humidified oxygen in oxygen outlet line 210. In some other embodiments, separate heat sources (which may be the same type or different) are used for heating the water and heating the humidified oxygen in oxygen outlet line 210.

FIGS. 3A and 3B depict humidification system 300, which is an embodiment of humidification system 100. Humidification system includes reservoir 302 and WVP membrane 206. Reservoir 302 comprises a soft, pliable, water-impermeable tube, such as, without limitation, a soft PVC tube. One end of WVP membrane 206 receives oxygen from a supply thereof (see, e.g., FIG. 1), and the other end is in fluidic communication with a nasal cannula (see, e.g., FIG. 1).

FIG. 3A depicts reservoir 302 full of liquid water 204, whereas FIG. 3B depicts the reservoir after a substantial amount of liquid water is lost; that is, evaporated and transported as water vapor into WVP membrane 206. FIG. 3B depicts the collapse of reservoir 302 due to the aforementioned loss of liquid water. Since reservoir 302 collapses, WVP membrane 206 remains in contact with liquid water, regardless of the spatial orientation (e.g., horizontal, vertical, etc.) of the humidification system.

FIG. 3C depicts humidification system 300', which is an embodiment of humidification system 100. In addition to reservoir 302 and WVP membrane 206 as in humidification system 300, system 300' includes oxygen outlet line 210, embodied as conduit 312. As in system 300', reservoir 302 comprises a soft, pliable, water-impermeable tube (e.g., a soft PVC tube, etc.) to facilitate collapse of the reservoir. In some embodiments, conduit 312 is a standard PVC oxygen line.

FIG. 3D depicts humidification system 300", which is yet another embodiment of humidification system 100. Humidification system 300" is similar to embodiments 300 and 300', and, again, reservoir 302 comprises a soft, pliable, water-impermeable tube to facilitate collapse of the reservoir. But humidification system 300" adds heating to reservoir 302 and oxygen outlet line 210.

In particular, web/tape 308 of heating wires embodies heating element 208 (FIG. 2). And oxygen outlet line 210, which in this embodiment is a "heated line," includes conduit 312, heating element 314, and insulation 316. In the embodiment depicted in FIG. 3D, heating element 314 is a wire that is disposed on the exterior of conduit 312, running lengthwise. In some other embodiments, the heating wire is wound spirally around conduit 312. In some further embodiments, the heating wire is embedded in (the wall of) conduit 312. In yet some additional embodiments, the heating wire is dispose inside (the lumen of) the conduit. In some embodiments, conduit 312 is a standard PVC oxygen line and insulation 316 is neoprene. Heated-line implementations of oxygen outlet line 210 are discussed in further detail later in this specification.

FIGS. 4A and 4B depict respective top and side views of humidification system 400, which is an embodiment of humidification system 100. In system 400, reservoir 202 and WVP membrane 206 are contained within housing 420. WVP membrane 206 is disposed in reservoir 202, such that the WVP membrane's exterior surface is exposed to liquid water 204. One end of WVP membrane 206 fluidically couples to oxygen inlet port 422 and the other end couples to oxygen outlet port 423. In this embodiment, oxygen outlet line 210, embodied as conduit 312, is fluidically coupled to oxygen outlet port 423, thereby placing the WVP membrane 206 and oxygen outlet line 210 in fluidic communication. In some otherwise identical embodiments, oxygen outlet line 210 is not included.

In the embodiment depicted in FIG. 4A and in other embodiments in this specification, WVP membrane 206 is implemented as a single tube. In some other embodiments, the WVP membrane can be implemented as two or more tubes. This may be desirable, for example, based on the form factor/size of the humidification system, or it may be required based on the material selected for use as the WVP membrane. In embodiments using more than one tube, the inlet and outlet ports can have multiple connections for coupling to such multiple tubes, or inlet and outlet headers can be used to accommodate multiple tubes.

The form factor of humidification system 400 enables it to be readily carried by a patient. In some embodiments, the humidification system is received in a carry case (not depicted), which couples to a patient's belt, or otherwise is supported by a waist- or shoulder strap. The form factor of humidification system 400 (in particular housing 420) is characterized by a thin, flat profile. In the illustrative embodiment, the form factor is further characterized as being quadrilateral; a rectangular or square shape. However, in some other embodiments, the shape is circular, oblong, oval, or the like. As used herein and the appended claims, the term "cartridge" is used to refer to embodiments of humidification system 100 in which the reservoir 202 and WVP membrane 206 are in a structure (e.g., housing 420, etc.) having a form factor as described above. In some embodiments, housing 420 (or other related embodiments of the housing/enclosure) has a length in the range of about 7.5 to about 13 cm, a width in the range of about 7 to about 10 cm, and a thickness in the range of about 1.25 to 2.5 cm. In some embodiments, housing 420 comprises a rigid material, such as, without limitation, an injection-molded plastic, including polyurethane and polypropylene, among others. Hereinafter, the terms "humidification system 400" and "cartridge 400" are used interchangeably.

FIGS. 5A and 5B depict respective top and side views of humidification system 500, which is an embodiment of humidification system 100. The salient elements of humidification system 500 include cartridge 400', receiver 530, and oxygen outlet line 210, which is embodied as a heated line. For clarity, certain elements (e.g., WVP membrane 206, etc.) depicted in FIG. 5A are not shown in FIG. 5B.

Cartridge 400' includes the same main elements (and has the same form factor) as humidification system 400, including WVP membrane 206 and reservoir 202 and functions in substantially the same manner. However, in this embodiment, heat is supplied to reservoir 202; in particular, via heating plate 508 of receiver 530.

FIGS. 5C and 5D depict respective top and side views of receiver 530, wherein the receiver is uncoupled to cartridge 400'. These figures depict latch 524, and heating plate 508, which in this embodiment is partially embedded in receiver 530.

In some embodiments, cartridge 400' is releasably secured to receiver 530, such as by latch 524. Heating plate 508 aligns with, and is in sufficient proximity to, reservoir 202 to be in thermal communication therewith when cartridge 400' and receiver 530 are coupled to one another. And when so coupled, heating plate 508 heats water 204 in reservoir 202, thereby controlling the level of humidification and the dew point of the oxygen flowing through WVP 206.

It will be appreciated that in the embodiment of humidification system 400 depicted in FIGS. 4A and 4B, the humidification system may include an outer housing, such as housing 420, that substantially completely encloses reservoir 202 (with the exception of the requisite oxygen inlet port 422 and outlet port 423 and certain other ports, etc.). However, for cartridge 400' depicted in FIGS. 5A and 5B, a housing that fully encloses the reservoir might not be acceptable, since the reservoir that is contained in the cartridge must be capable of efficiently receiving heat from heating plate 508 of receiver 530.

To this end, in some embodiments of cartridge 400' depicted in FIGS. 5A and 5B, surface 525 of reservoir 202 (the "lower" surface of the reservoir, which is proximal to heating plate 508) is in direct contact with heating plate 508. In other words, there is an opening in housing 420' between heating plate 508 and lower surface 525 of the reservoir such that a portion of reservoir 202 abuts heating plate 508. (A gap between the heating plate and reservoir is depicted in FIG. 5B for clarity.)

FIG. 5E depicts an embodiment of housing 420', wherein the housing includes opening 527, which is dimensioned and arranged so that substantially all of the surface area of lower surface 525 of reservoir 202 is in contact with heating plate 508 when cartridge 400' and receiver 530 are coupled to one another. To enable cartridge 400' to be used without receiver 530 (such as for periods of time when reservoir heating is not necessary or must be dispensed with for convenience), removable cover 528 can be coupled to the "lower" surface of housing 420', covering opening 527. With cover 528 attached, housing 420' is essentially identical to housing 420 of humidification system 400. Cover 528, which can attach to housing 420' via press fit, hook and loop fastener, or other conventional means, is recommended for use when the cartridge 400' is being used without receiver 530 since, if the material that forms lower surface 525 of reservoir 202 were exposed to the external environment, it could be pierced, causing leakage of water. In some other embodiments (not depicted), rather than having opening 527, housing 420' is structured so that it only has an upper surface and four sides, wherein there is no "bottom" surface.

In yet some other embodiments, such as depicted in FIG. 5F, housing 420" substantially fully encloses reservoir 202. However, rather than being formed from a single material, such an injection-molded plastic, housing 420" includes portion 529 comprising a material having a high thermal conductivity, such as, for example and without limitation, a metal (e.g., copper, aluminum, etc.) or a thermally conductive plastic, such as THERMA-TECH™ brand thermally conductive plastic available from PolyOne Corp of Avon Lake, Ohio or COOLPOLY® brand thermally conductive plastic available from Celanese Corp of Dallas, Tex. Portion 529 is inlaid, embedded, inserted, etc., in housing 420" in the region that aligns with heating plate 508, facilitating the transfer of heat from heating plate 508 to water 204 in reservoir 202. As used herein, the term "high thermal conductivity material" means a material having a thermally conductivity at least 5 times higher than that of conventional, "unfilled" plastics (which typically have a thermal conductivity of about 0.2 W/mK). In embodiments in which thermally conductive plastic is used, the thermally conductive plastic preferably has a thermally conductivity of at least 10 W/mK, and more preferably at least 50 W/mK.

With continuing reference to FIG. 5A, since humidification system 500 includes a capability for heating water 204 in reservoir 202, oxygen outlet line 210 should be a heated line (i.e., to prevent rain out in the line/nasal cannula). To that end, oxygen outlet line 210 includes conduit 312, heating element 314, and insulation 316. As previously discussed, in some embodiments, conduit 312 is a standard PVC oxygen line, insulation 316 comprises neoprene, and heating element 314 is a wire that is disposed on the outside surface of conduit 312, running longitudinally therewith.

In some alternative embodiments, heating element 314 may be spirally wound around conduit 312. Or, heating element 314 is a heating tape that is spirally wound around conduit 312. The spirally wound configuration is useful, for example, in situations in which relatively longer lengths of heating element 314 are required to achieve the requisite heating wattage. On the other hand, a benefit to the use of a longitudinal heating element is that the heat applied per unit length is constant. With a spirally wound configuration, variation in the spacing of spirals results in regions receiving relatively greater or lesser amounts of heat.

In yet in some further embodiments, heating element 314 can be embedded in the wall of conduit 312 or disposed within the lumen of conduit 312. In some embodiments, heating element 314 comprises carbon fiber wire. Further description of heating element 314 and the manner in which it is interconnected to other elements of the humidification system is provided later in this specification in conjunction with FIG. 10A.

Insulation 316 provides several benefits, including uniformly spreading the heat generated from heating element 314, significantly reducing the power required to heat the line (by minimizing heat loss), and it is comfortable against a user's skin.

Figure 11A:
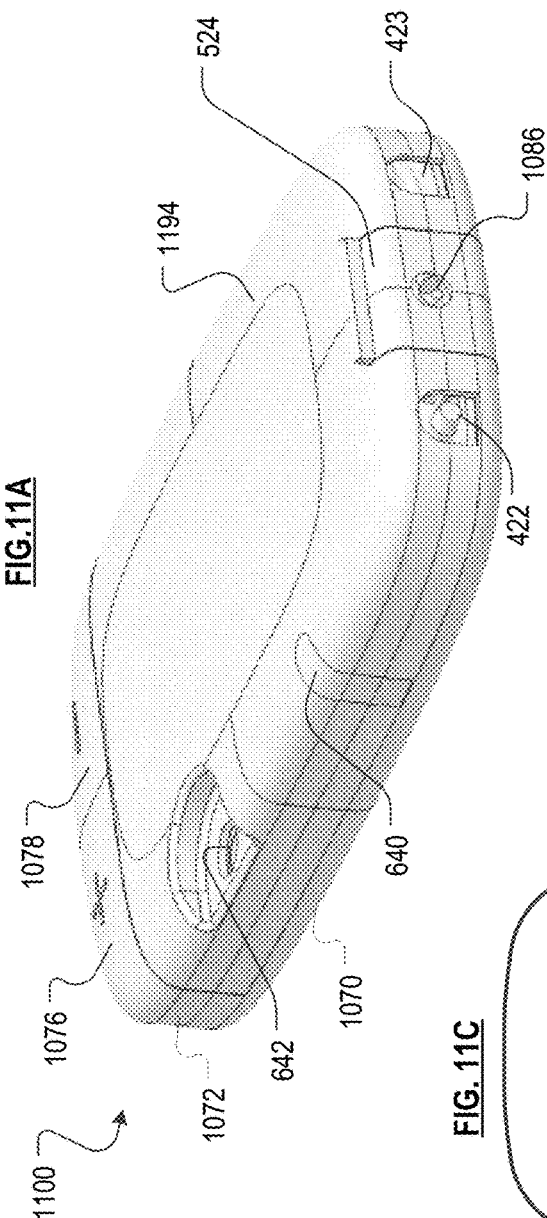
FIG. 11A depicts a top perspective view of an embodiment of humidification system 1100, which is an embodiment of humidification system 500, the view showing a first end and a first side of the humidification system.
Figure 11B:
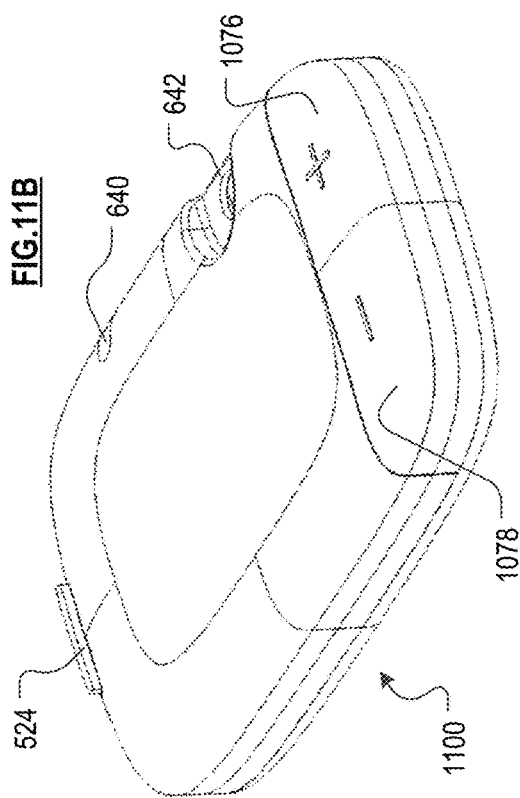
FIG. 11B depicts a top perspective view of humidification system 1100, the view showing a second end and second side of the system.
Figure 11C:
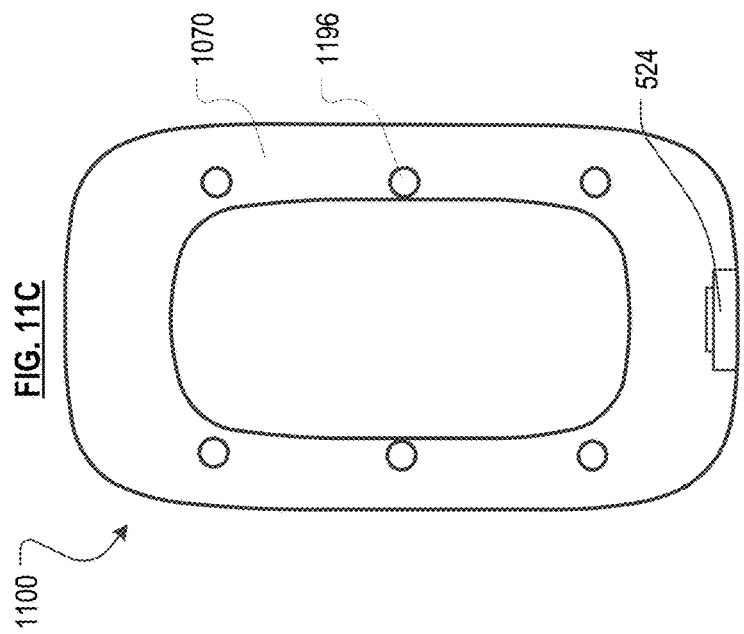
FIG. 11C depicts a bottom view of humidification system 1100.

FIGS. 6A through 6F depict an embodiment of internal elements (i.e., the elements within a protective housing, such as housings 420, 420', 420") of some embodiments of humidification systems having a "cartridge" form factor, such as systems 400, 500, 800 (FIG. 8), and 1100 (FIGS. 11A-11C).

The embodiment depicted in these figures, and with particular reference to FIG. 6A, includes frame 631, which, like a picture frame, has an open central region, identified in the figures as region 636. In some embodiments, frame 631 comprises an injection-molded plastic, such as polyurethane, polypropylene, etc.

A plurality of retainers 638 extend inwardly into region 636. In some embodiments, retainers 638 are coupled to frame 631. More particularly, in some embodiments, retainers 638 attach directly to frame 631; in some other embodiments, the retainers are attached to a fixture (not depicted) that attaches to frame 631. In some embodiments, the fixture has the same shape as the frame, and has dimensions suitable for overlying (or underlying) frame 631. Retainers 638 receive WVP membrane 206 and maintain it in a predefined position. As depicted in FIGS. 6C through 6F, in some embodiments, the predefined position of WVP membrane 206 is proximal to the "bottom" of the reservoir. The retainers are thus another structural adaptation that, in conjunction with the collapsibility of the reservoir, ensures that WVP membrane 206 remains at least partially in contact with liquid water regardless of the orientation of reservoir/cartridge.

With continuing reference to FIG. 6A, an impermeable film or membrane 650 is coupled to "top" surface 634 of frame 631 and an impermeable film or membrane 652 is coupled to "bottom" surface 632 of the frame. (For clarity, only a small portion of these membranes are depicted in FIG. 6A.) In some embodiments, these membranes are attached directly to frame 631; in some other embodiments, the membranes are attached to the aforementioned fixture. In some embodiments, attachment is effected via ultrasonic welding. FIG. 6B depicts the full membrane 650 attached to frame 631, "overlying" WVP membrane 206 (which is obscured in FIG. 6B).

As depicted most clearly in FIGS. 6C through 6F, membranes 650 and 652, in conjunction with open region 636 as well as the inner surfaces of frame 631, collectively form reservoir 402, which is an implementation of reservoir 202. In some embodiments, both impermeable membranes 650 and 652 comprise urethanes.

In the illustrative embodiment, "lower" impermeable membrane 652 remains flat (i.e., parallel to the bottom 632 of frame 631), whereas impermeable membrane 650 must be able to move towards or away from membrane 652. This enables the volume of reservoir 402 to expand or contract with changes in the amount of water 204 therein. In some embodiments, upper membrane 650 is vacuum formed to provide it with the requisite surface area to move. Since, in the illustrative embodiment, membranes 650 and 652 are formed from a resilient material having a limited ability to "stretch," there is more of membrane 650 than there is of membrane 652 within open central region 636. This is seen most clearly in FIGS. 6D through 6F.

As depicted in FIG. 6D, when there is a maximum amount of water 204 in reservoir 402, membrane 650 rises above upper surface 634 of frame 631 to accommodate the water. When, as depicted in FIG. 6E, there is a minimal amount of water 204 in the reservoir, membrane 650 drops below upper surface 634 of frame 631 towards membrane 652 to maintain contact with the surface of the water. This keeps at least a portion of the overall exterior surface area of WVP membrane 206 in contact with liquid water. FIG. 6C depicts reservoir 402 containing an intermediate amount of water, wherein membrane 650 is effectively coplanar with upper surface 634 of frame 631. Thus, in the illustrative embodiment, the position of membrane 650 is fully variable between upper and lower extremes, appropriately altering the effective volume of reservoir 402 to accommodate the change in the volume of water 204 therein (due to evaporation and subsequent transport into WVP membrane 206).

FIG. 6F depicts reservoir 402 in a "vertical" position, such as if it were being carried against a patient's body, rather than resting on a surface (e.g., table, etc.), and with minimal water 204 therein. Because WVP membrane 206 is maintained in a predefined position—for example, proximal to membrane 652—by virtue of retainers 638, and because reservoir 402 is collapsible, WVP membrane 206 remains in contact with the liquid water in the reservoir.

Returning to FIG. 6A, this embodiment also includes oxygen inlet port 422, oxygen outlet port 423, water gauge 640, thermostat 644, fill port 642, circuit board 646, and optional power supply 648.

WVP membrane 206, embodied as a flexible tube, is coupled at one end to oxygen inlet port 422 and at its other end to oxygen outlet port 423. The oxygen inlet port 422 is also connected to an oxygen line (not depicted) that conveys oxygen from oxygen source 90 (FIG. 1). And oxygen outlet port 423 is also connected to an oxygen outlet line, such as oxygen outlet line 210. Thus, oxygen flows through the interior of WVP membrane 206 while the exterior of the tube is exposed to water 204. The water level in reservoir 402 is observable via water gauge 640, which can be embodied as a simple sight gauge with a ball-float indicator.

Fill port 642 enables reservoir 402 to be filled/refilled with water. In some embodiments, fill port 642 is implemented as a Luer fitting, which receives a corresponding dispensing Luer fitting for dispensing water 204. In some embodiments, fill port 642 comprises a valve to prevent air or contaminants from entering when the corresponding dispensing Luer fitting is not present. A non-limiting example of such a valve is a needlefree swabable valve as is commercially available from Nordson Medical of Westlake, Ohio. In this regard, a large "syringe" or small accordion bottle filled with distilled or de-ionized water can be provided for use with such an embodiment of the humidification system. After the initial dose of water is introduced into reservoir 402 and humidifies the flowing oxygen, the syringe or bottle can be refilled with distilled/de-ionized water and engaged to the fill port 642 to refill reservoir 402.

In some embodiments, fill port 642 can be used to extract air that might enter reservoir 402', as well as to fill the reservoir with water. In such an embodiment, air is directed to fill Port 642 by appropriately orienting the reservoir. After filling the reservoir with water, the syringe or bottle can be used to extract air, as appropriate.

In some embodiments, a pump (not depicted) is used in conjunction with fill port 642 to supply water to reservoir 402. In some of such embodiments, the pump is a manual pump, with each stroke providing a predetermined amount of water. To avoid over-pressurizing or over-filling reservoir 402, in some embodiments, a pressure relief valve is incorporated into the pump, wherein any additional pumps of water are redirected back to the water source (i.e., external water container). In some other embodiments, the pump is electrically driven and controlled. The pump control can be used to automatically shut-off when the pressure reaches a threshold value, or a bypass feature can be used.

In yet some further embodiments, the pump can connect to two ports with two separate lines; a fill port with a fill line and a return port (not depicted) with a return line. The fill port (e.g., fill port 642, etc.) is used to supply water to reservoir 402. The return port is positioned such that in the normal fill orientation, the return port is located at the highest location in reservoir 402. This will place the return port in contact with any air that might be in the reservoir, and return that air to the fill container during the fill cycle. Once all air is purged, water will start flowing through the return path, which will then signal the user that it is time to stop pumping. This accomplishes the objective of removing air from the reservoir to keep the WVP membrane in contact with liquid water, and prevents over-filling or over-pressurizing the reservoir since excess water will simply return to the container that is the source of the water.

In still some further embodiments, fill port 642 is fluidically coupled to a much larger (than reservoir 402) container of water, such as a sterile water bag to provide, thereby providing a much larger water capacity. In embodiments in which the WVP membrane comprises Nafion™, the pressure of the water has very little if any effect on performance. As such, a simple collapsible bag, positioned anywhere above reservoir 402, will continuously flow water into the reservoir as the liquid water therein evaporates and passes into the oxygen flowing through the WVP membrane. This arrangement is particularly advantageous in acute-care settings wherein oxygen therapy is applied continuously for long periods of time to an immobile patient.

Additional elements depicted in FIG. 6a, such as thermostat 644, circuit board 646, and optional power supply 648, are described later in this disclosure.

Figure 7A:
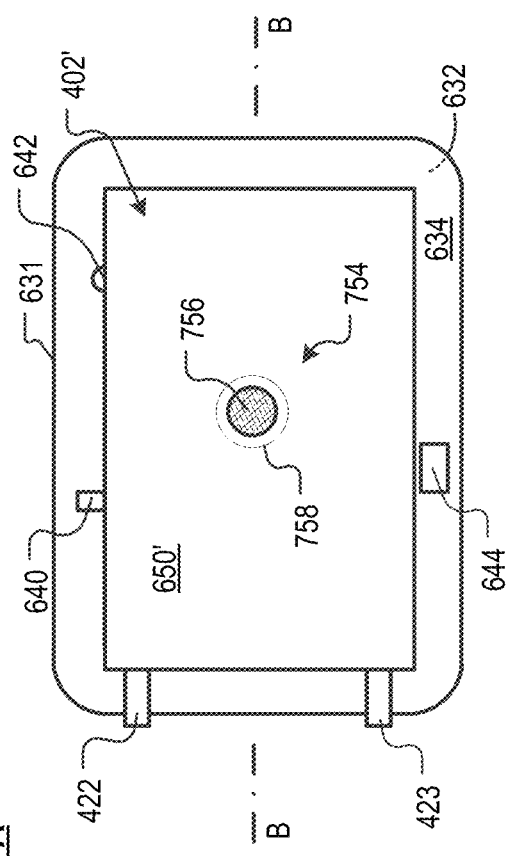
FIGS. 7A and 7B depict respective top and cross-sectional views of a further embodiment of a reservoir.
Figure 7B:
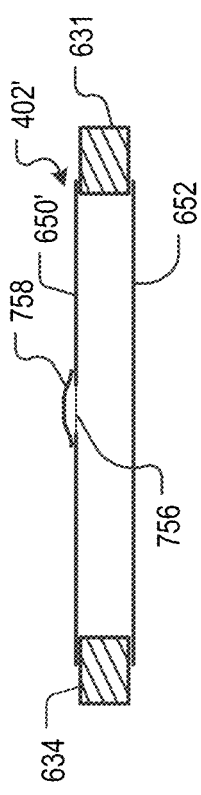

FIGS. 7A and 7B depict respective top view and sectional views (at line B-B) of reservoir 402' (with certain internal elements, such as WVP membrane 206, etc., omitted for clarity). In this embodiment, the reservoir includes vent 754, which is incorporated in upper membrane 650'. This vent is yet another structural adaptation that facilitates the collapsibility of a reservoir for use in conjunction with some embodiments of the invention. The purpose of the vent is to enable any air that might enter reservoir 402' to escape, while preventing the loss of liquid water from the reservoir.

In the embodiment depicted in FIGS. 7A and 7B, vent 754 comprises liquid-water impermeable (but gas permeable) barrier 756 and valve 758. In some embodiments, barrier 756 comprises a fabric, formed from high-density polyethylene fiber or stretched polytetrafluoroethylene, non-limiting examples of which are commercially available from DuPont under the brand name Tyvek®, or from W.L. Gore and Associates under the brand name Gore-Tex®.

Valve 758 functions as a one-way check valve, moving "upward" (i.e., away from membrane 650') under the influence of positive pressure (i.e., higher pressure in reservoir 402'). Valve 758 serves to prevent gas (or liquid) from entering the reservoir, and also functions to limit, to the extent possible, water-vapor loss through vent 756.

In the illustrative embodiment, valve 758 is a mini umbrella valve, which has a convex diaphragm-shaped sealing disk that seals against negative pressure (i.e., lower pressure in reservoir 402' than surrounding environment), but lifts and unseals against positive pressure (i.e., relatively higher pressure in reservoir 402' than surrounding environment). Such a valve is available from miniValve Inc of Cleveland, Ohio, or others. In some other embodiments, a thin-film check valve that relies on surface-to-surface affinity to stick the valve sheet to membrane 650' to prevent air from entering reservoir 402' while enabling air to escape. Such a valve is commercially available from Dielectrics Industries of Chicopee, Mass. Valve 448 comprises, in some embodiments, the same material as membrane 340 (e.g., urethane, etc.).

FIG. 8 depicts humidification system 800, which is a further embodiment of humidification system 100. The salient features of system 800 include, in addition to the elements present in other embodiments discussed herein (e.g., reservoir 202, WVP membrane 206, an enclosure or housing, such as housing 420, 420', or 420", etc.), means 860 for applying positive pressure to the upper surface of reservoir 202. This is a further structural adaptation that may be used to promote collapse of reservoir 202 so that WVP membrane 206 remains in contact with liquid water.

In the embodiment depicted in FIG. 8, means 860 for applying positive pressure to reservoir 202 includes pressure plate 862 and resilient elements 864. The resilient elements are preloaded by compressing them between pressure plate 864 and the inside of the housing. The resilient elements therefore apply a force against pressure plate 864. Because liquid water is non-compressible, the water resists the applied pressure. However, as water evaporates and passes into WVP membrane 206, the pressure applied against reservoir 202 ensures that the volume of the reservoir will be no greater than is required to accommodate the remaining water. This is particularly useful for maintaining minimum reservoir volume when the reservoir is in a vertical or otherwise not horizontal orientation.

In the illustrative embodiment, resilient elements 864 are springs. In some other embodiments, the resilient elements can be a resilient material, such as rubber, etc. In some embodiments, rather than having a plurality of discrete elements, a sheet of rubber or other resilient material is placed between pressure plate 862 and the inside surface of housing 420, 420', 420". In embodiments in which reservoir 202 includes a vent and/or fill port, accommodation must be made for such features, such as by providing suitably positioned and sized openings in pressure plate 862.

Figure 9A:
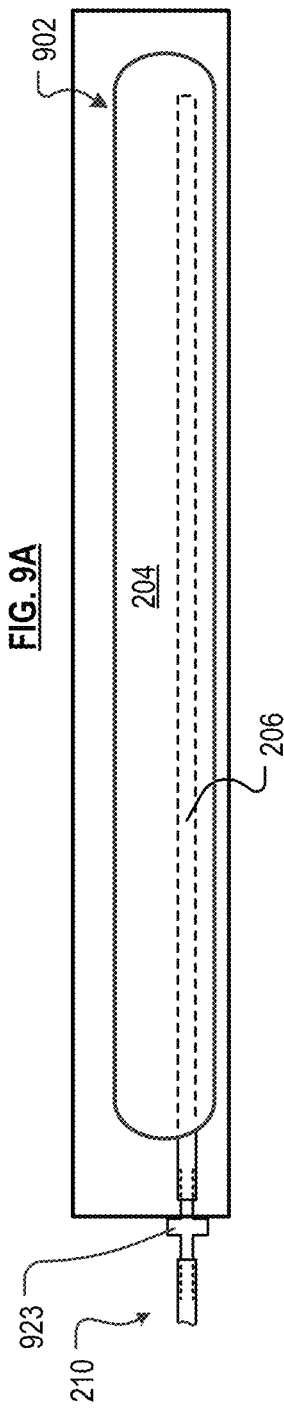
FIG. 9A depicts a side view of reservoir 902, which is an embodiment of reservoir 202.

FIG. 9A depicts reservoir 902, which is another embodiment of reservoir 202. In this embodiment, the reservoir is in the form of a bag or pouch. Most of WVP membrane 206 is contained within reservoir 902. In this embodiment, a short length of the WVP membrane near both ends thereof extends beyond the confines of reservoir 902 to couple to the fittings. (Only one end—the outlet—is depicted; the inlet is obscured.) For example, the outlet end of WVP membrane 206 couples to fitting 923, which is an embodiment of oxygen-outlet port 423. Oxygen outlet line 210 also couples to fitting 923, such that humidified oxygen from WVP membrane 206 flows to oxygen outlet line 210 and then to a patient. In some embodiments, fitting 923 removably couples to reservoir 902 to facilitate replacing WVP membrane 206 without replacing the reservoir itself. In some embodiments, reservoir 902 includes a vent (not depicted in FIG. 9A), such as vent 754 (FIGS. 7A and 7B).

Reservoir 902 can be single use. When the water in the reservoir drops to a threshold amount (previously discussed), reservoir 902 is replaced with another reservoir 902 that is full of water. In some embodiments, arrangement 860 for applying positive pressure is used to promote collapse of reservoir 902 as water evaporates and passes into WVP membrane 206.

Figure 9B:
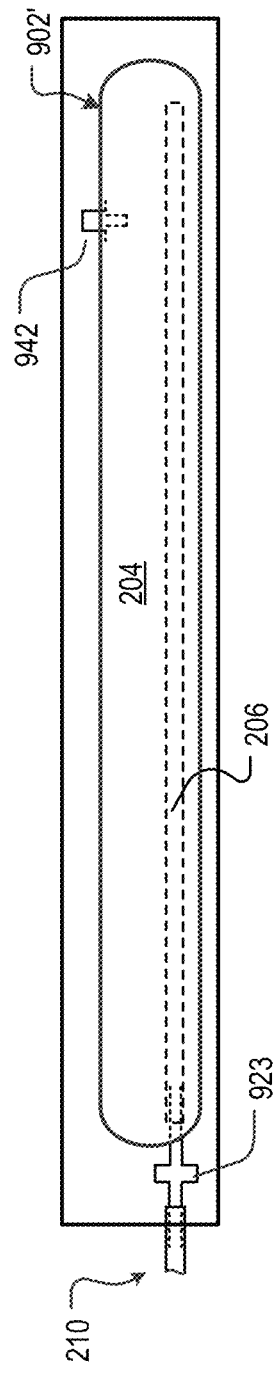
FIG. 9B depicts a side view of reservoir 902', which is another embodiment of reservoir 202.
Figure 9C:
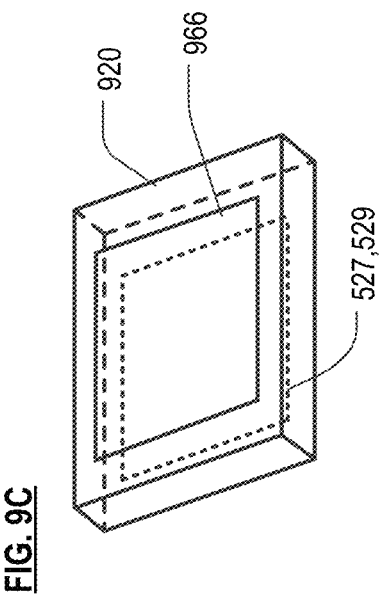
FIG. 9C depicts a perspective view of housing 920 for use with reservoirs 902 and 902'.

FIG. 9B depicts reservoir 902', which is yet an additional embodiment of reservoir 202. Like reservoir 902, reservoir 902' is in the form of a bag or pouch. However, unlike reservoir 902, all of WVP membrane 206 is contained within reservoir 902. Rather, fitting 923 extends through the wall of reservoir 902' for coupling to oxygen outlet line 210. In some embodiments, reservoir 902' includes a vent (not depicted in FIG. 9B), such as vent 754 (FIGS. 7A and 7B). Unlike reservoir 902, reservoir 902' is refillable via fill port 942. In some embodiments, fill port 942 is implemented as a Luer lock.

To readily replace and/or access reservoirs 902 and 902', in some embodiments, housing 920 is used in conjunction with such reservoirs. Housing 920 includes removable cover 966, which provides access to the inside of the cartridge. In the illustrative embodiment, housing 920 is depicted as including opening 527 or thermally conductive insert 529, such as is used for some embodiments of the humidification system in which the reservoir is heated. In some other embodiments, such as when heating is not desired or not required, such opening or insert can be omitted (see, e.g., humidification system 400).

In some embodiments in which reservoir 202 is in the form of a bag/pouch, such as reservoirs 902 and 902', the bag/pouch is made from a single material, such as, for example, urethane or silicone.

As previously mentioned, to ensure best performance, reservoir 202 should be discarded after a period of time. In some embodiments, such as at least some of those in which reservoir 202 is embodied as a bag or pouch (see, e.g., FIGS. 9A, 9B), the reservoir may be removable from the surrounding housing. In some other embodiments, such as the embodiment depicted in FIGS. 6A through 6F, and in FIGS. 7A and 7B, the complete cartridge (e.g., cartridge 400', etc.) is replaceable and considered to be a "consumable." Also, to the extent it is included in any given embodiment, oxygen outlet line 210 is typically replaced when the reservoir/cartridge is replaced.

Figure 10A:
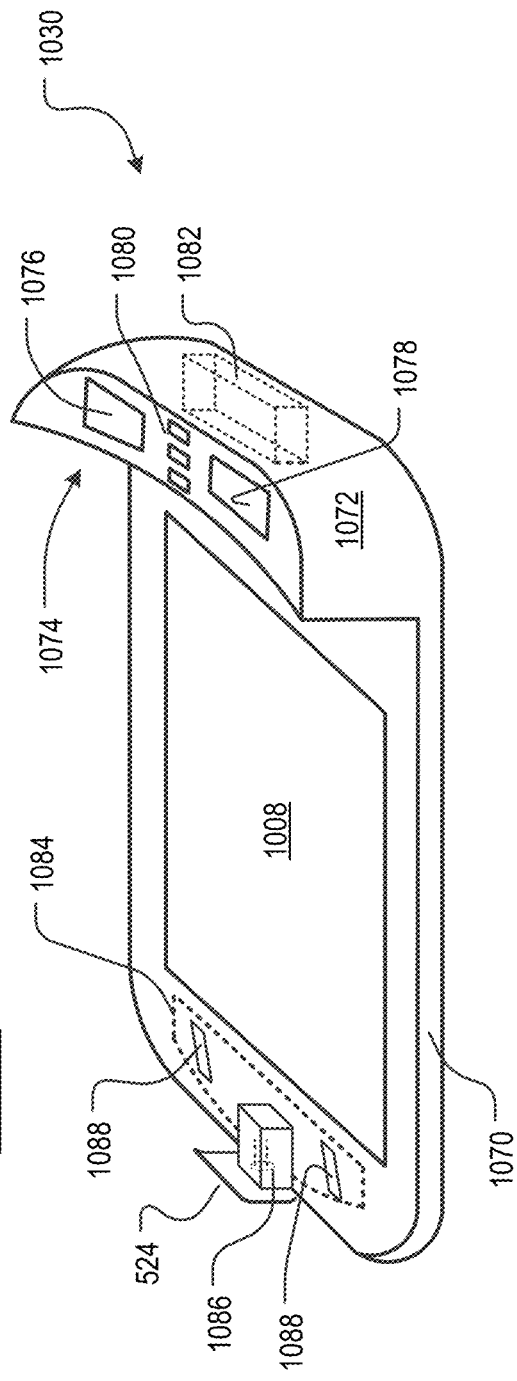
FIG. 10A depicts a perspective view of receiver 1030, which is an embodiment of receiver 530 of humidification system 500.
Figure 10B:
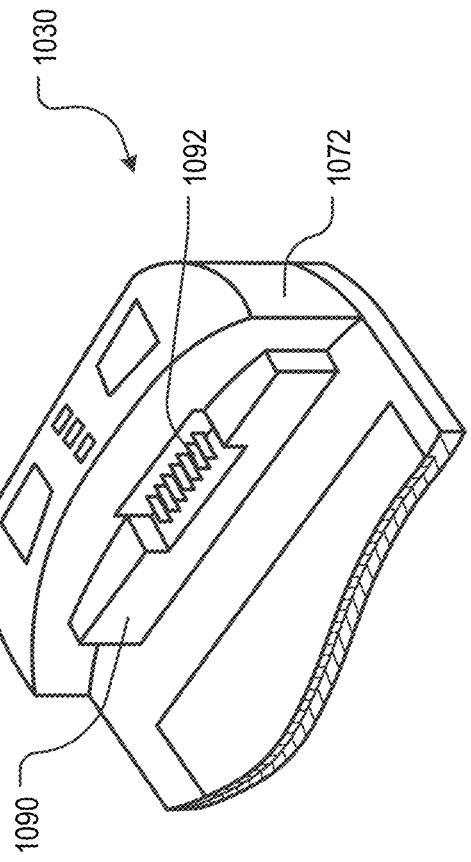
FIG. 10B depicts a partial perspective view of receiver 1030.

FIGS. 10a and 10B depict receiver 1030, which is an embodiment of receiver 530 of humidification system 500. The receiver includes base 1070, heating plate 1008, control portion 1072, control panel 1074, optional power supply 1082, electronics board 1084, power input 1086, optional spring contacts 1088, boss 1090, and optional electrical contacts 1092.

Base 1070 is dimensioned and arranged to receive/align cartridge 400' (or other versions thereof) as depicted in FIGS. 5A and 5B, and to facilitate humidification operations.

As to alignment, boss 1090 (FIG. 10B) aligns and stabilizes cartridge 400' on receiver 1030 and supports optional electrical contacts 1092. With respect to humidification operations, heating plate 1008, which is partially embedded in base 1070, aligns with membrane 652 of reservoir 402, 402', etc., when the cartridge and receiver 1030 are coupled. So aligned, heating plate 1008 heats water 204 in the reservoir, thereby controlling the level of humidification and the dew point of the oxygen.

Heating plate 1008, which in some embodiments comprises aluminum, is resistively heated by current sourced from an external source of power (e.g., AC power, as appropriately converted to DC and reduced in voltage, a battery, etc.), as coupled through power input 1086, or from optional on-board power supply 1082 (e.g., rechargeable or non-rechargeable battery, super capacitor, etc.).

Control panel 1074 includes user-operated controls for controlling the level of heating (i.e., humidification) as well as status indicators. In the embodiment depicted in FIGS. 10A and 10B, user controls include buttons 1076 and 1078. Pressing button 1076, for example, increases the level of heating (humidification) while pressing button 1078 decreases it. In some embodiments, when pressed, buttons 1076 and 1078 abut contact switches (not depicted) under control panel 1074, which signal electronics board 1084. In some other embodiments, other control devices as commonly used for such applications, such as a rotary switch, etc., with appropriate electrical connections to electronics board 1084, are suitably be used for controlling heating plate 1008.

In some embodiments, the heating levels provided by receiver 1030 are discrete; for example, heating plate 1008 can be controlled to a few different temperatures, such as 28° C., 32° C., and 36° C. In such embodiments, indicators, such as indicator lights 1080 (e.g., LEDs, etc.), may be used to indicate the level of heating (humidification) provided. For example, one light illuminated for low-level heating/humidification (e.g., 28° C.), two lights illuminated for a moderate level (e.g., 32° C.), and three lights illuminated for a high level (e.g., 36° C.).

In some other embodiments, heating/humidification is analog; that is, infinitely controllable between a low and high value. In some embodiments, a temperature gauge is included on control panel 1074. As previously discussed, in some embodiments, oxygen outlet line 210 is heated, and, in some such embodiments, control panel 1074 includes a control device for controlling the temperature of that line.

Electronics board 1088, which includes one or more processors, memory, etc., is suitably programmed to maintain temperature within safe operating ranges to prevent injury to the patient. In some embodiments, the electronics board, in conjunction with appropriate sensors, is capable of identifying and signaling power outages, flow restrictions, low oxygen flow, high or low temperatures or other faults. Oxygen flow sensors, for example, may be used to prevent oxygen deprivation, even in situations in which the humidifier itself is not at fault (e.g., the oxygen cylinder running out of oxygen, etc.). Resistance sensing on the heating elements can sense electrical shorts and prevent unsafe operation in case of a mechanical fault. Ambient temperature sensing can detect when the ambient temperatures are above 37° C. and shut down heating to prevent over humidification of the oxygen stream. Indicator lights 1080, for example, can be used to indicate such conditions, by "blinking" in a particular pattern.

To the extent power is coupled between receiver 1030 and a cartridge (e.g., cartridge 400'), such as for heating outlet-oxygen line 210, electrical contacts 1092 can be used to do so. Additionally, the electrical contacts can be used to read an identifier associated with the cartridge. From this information, and information stored in memory on electronics board 1084 (e.g., usage, age, etc.), receiver 1030 can signal replacement of the cartridge and/or reservoir as appropriate, as well as providing additional information to the user and/or manufacturer.

In some embodiments, particularly those in which there is relatively minimal coupling of power and signals between receiver 1030 and cartridge 400', spring contacts 1088 can be used rather than optional contacts 1092.

As previously noted, in some embodiments, heating element 314 comprises carbon fiber wire. Referring again to FIG. 5A, at the distal end of conduit 312 (i.e., the end closest to the patient), the carbon fiber wire is electrically coupled to a "return" wire (not depicted), such as a standard copper wire (e.g., 28 gauge) via a standard electrical crimp connector. A spade connector (not depicted) disposed at the end of heating element 314 nearest cartridge 400' and a spade connector (not depicted) disposed at the end of the return wire (not depicted) nearest cartridge 400' are electrically coupled to base 1030 via, for example, spring contacts 1088 (FIG. 10A). In such an embodiment, receiver 1030 provides power to heating element 314 and the current in the return line is measured to determine wire resistance. The resistance can then be used to control the temperature of oxygen outlet line 210 in known fashion.

With continued reference to FIG. 10A, and returning to FIG. 6A, rather than sourcing power from receiver 1030, the power for oxygen outlet line 210 (when heated) can be sourced from optional power supply 648 in cartridge 400'. Thermostat 644 is used to stop the flow of current to line 210 if temperature exceeds a set point. Circuit board 646 controls the amount of power supplied to line 210 or directly controls the temperature by measuring the resistance of the heating wire 314.

FIGS. 11A through 11C depict humidification system 1100, which is another embodiment of humidification system 100, and, in fact, is a specific implementation of humidification system 500 (depicted in FIGS. 5A and 5B, sans oxygen outlet line 210). FIGS. 11A and 11B depict perspective views of the "upper" surface of humidification system 100 from different ends thereof. These figures depict various elements presented in previous drawings and the accompanying description.

Humidification system 1100 is very compact and is based on the cartridge form factor. FIGS. 11A and 11B depict housing 1194, which is an embodiment of housings 420, 420', 420", and 920. These figures depict latch 524, power port 1086, oxygen inlet port 422, humidified oxygen outlet port 423, sight gauge 640, fill port 642, base 1070, control portion 1072, and user temperature/humidity controls 1076 and 1078.

FIG. 11C depicts a "bottom" view of humidification system 1100. A plurality of feet 1196, which may comprise a foam material, are disposed on bottom of base 1070. The lower portion of latch 524 is visible on bottom of base 1070. It is noted that a number of lines appearing in FIGS. 11A through 11C are "contour" lines; they are not actually present, they are shown to illustrate surface contours.

Definitions. The following definitions, in addition to those previously provided in context, are to be used to interpret terms used in this disclosure and the appended "about" or "substantially" means within +/−15% of a stated figure.

"up", "down", "lower", "upper", "below", "above" are used to reference positions depicted in drawings, and do not have any absolute meaning. That is, they reference a position based on a particular orientation of the humidification system (horizontal, vertical, etc.), as depicted in the Figures. However, one skilled in the art will be able to discern, in absolute terms, the position of such elements with respect to other elements, based on such descriptors.

It is to be understood that the disclosure describes a few embodiments and that many variations of the invention can easily be devised by those skilled in the art after reading this disclosure and that the scope of the present invention is to be determined by the following claims.

What is claimed:

1. A humidification system for use with low-flow oxygen therapy, the humidification system comprising:
   a reservoir, wherein the reservoir receives a volume of liquid water, and further wherein a liquid capacity of the reservoir is alterable such that instantaneous liquid capacity of the reservoir is substantially equal to an instantaneous volume of liquid water in the reservoir; and
   a tube comprising a water-vapor-permeable (WVP) membrane, wherein a major portion of the tube is contained in the reservoir.

2. The humidification system of claim 1 wherein the WVP membrane comprises a perfluorosulfonic acid polymer.

3. The humidification system of claim 1 wherein the reservoir comprises two spaced-apart liquid-water-impermeable membranes, wherein a first one of the two membranes comprises a greater surface area than a second one of the two membranes.

4. The humidification system of claim 1 wherein the reservoir comprises a pouch.

5. The humidification system of claim 1 wherein the reservoir comprises a tube comprising a soft, pliable material.

6. The humidification system of claim 1 wherein the reservoir comprises a vent.

7. The humidification system of claim 1 and further comprising means for applying positive pressure to the reservoir.

8. The humidification system of claim 1 and further comprising one or more restraints that immobilize the tube within the reservoir.

9. The humidification system of claim 1 and further comprising a heater for heating the liquid water in the reservoir.

10. The humidification system of claim 1 and further comprising an oxygen outlet line coupled to an end of the tube.

11. The humidification system of claim 10 and further comprising a heating element for heating the oxygen outlet line.

12. The humidification system of claim 1 wherein the reservoir and the tube are contained in housing, wherein the housing, reservoir, and tube collectively define a cartridge.

13. The humidification system of claim 12 and further comprising a receiver, wherein the receiver includes a heater, and wherein the receiver and the cartridge are physically adapted to couple to one another, and when coupled, the heater aligns with and is in sufficient proximity to the reservoir to heat the water therein.

14. The humidification system of claim 13 wherein the housing of the cartridge includes an opening, wherein the opening is located so that the heater abuts a portion of the reservoir when the receiver and the cartridge are coupled to one another.

15. The humidification system of claim 14 wherein the housing further comprises a cover that detachably couples to the housing at the opening.

16. The humidification system of claim 13 wherein at least a portion of the housing comprises a high-thermal-conductivity material, wherein the portion is located between the reservoir and the heater when the receiver and the cartridge are coupled to one another.

17. The humidification system of claim 13 wherein the receiver includes a user interface by which a user adjusts the temperature of the reservoir.

18. The humidification system of claim 1 wherein the reservoir comprises a fill port for filling the reservoir with water.

19. The humidification system of claim 18 further comprising a pump for pumping the water into the reservoir through the fill port.

20. The humidification system of claim 19 and further comprising a source of water for filling the reservoir, wherein the reservoir is fluidically coupled to the source of water via the pump.

21. The humidification system of claim 20 wherein the water reservoir further comprises a return port, wherein, in conjunction with a return line, the return port fluidically couples the reservoir to the source of water.

22. The humidification system of claim 18 further comprising a sterile water bag, wherein the sterile water bag is fluidically coupled to the fill port to provide a continuous supply of water to the reservoir.

23. The humidification system of claim 13 wherein receiver includes a power inlet port.

24. The humidification system of claim 9 further comprising a power source.

25. The humidification system of claim 12 wherein the cartridge includes an identifier, wherein the identifier is electronically read.

26. The humidification system of claim 12, wherein the housing has a length of about 13 centimeters and a width of about 10 centimeters.

27. The humidification system of claim 17 wherein the user interface is operable to control the temperature of the reservoir to at least one of 28° C., 32° C., and 36° C.

28. The humidification system of claim 9 wherein the heater is physically adapted to enable resistance heating thereof.

29. A humidification system for use with low-flow oxygen therapy, the humidification system comprising:
   a housing;
   a water reservoir contained in the housing, wherein the water reservoir is refillable, and further wherein a volume of the reservoir adapts to an amount of liquid water contained therein;
   a tube comprising a water-vapor-permeable (WVP) membrane, wherein a major portion of the tube is contained in the water reservoir, wherein the housing, the water reservoir, and the tube collectively define a cartridge;
   a receiver, the receiver including a heating element, and wherein the cartridge and the receiver are structured for detachable coupling with one another, wherein, when coupled, the heating element transfers heat to the reservoir.

* * * * *